United States Patent [19]

Fest et al.

[11] 4,318,924

[45] Mar. 9, 1982

[54] COMBATING BACTERIA WITH N-CYCLOALKYL-N'-SUBSTITUTED-N'-ACYL-UREAS

[75] Inventors: Christa Fest, Wuppertal; Peter Kraus, Cologne; Hans Scheinpflug, Leverkusen, all of Fed. Rep. of Germany

[73] Assignee: Bayer Aktiengesellschaft, Leverkusen, Fed. Rep. of Germany

[21] Appl. No.: 141,832

[22] Filed: Apr. 21, 1980

[30] Foreign Application Priority Data

May 12, 1979 [DE] Fed. Rep. of Germany ....... 2919292

[51] Int. Cl.[3] ..................... A01N 47/28; C07C 127/00

[52] U.S. Cl. ...................................... 424/322; 564/44; 564/45; 564/57

[58] Field of Search .................... 424/322; 564/44, 45, 564/57

[56] References Cited

U.S. PATENT DOCUMENTS

| | | | |
|---|---|---|---|
| 3,384,473 | 5/1968 | Pillon et al. | 564/44 |
| 3,821,305 | 6/1974 | Bartalini et al. | 260/583 K |
| 3,845,086 | 10/1974 | Marsh | 424/322 |
| 3,957,756 | 5/1976 | Ribka et al. | 564/44 |
| 4,013,706 | 3/1977 | Anatol et al. | 260/471 C |
| 4,013,717 | 3/1977 | Wellinga et al. | 564/44 |
| 4,101,575 | 7/1978 | Enders et al. | 424/322 |
| 4,277,499 | 7/1981 | Sirrenberg et al. | 424/322 |

FOREIGN PATENT DOCUMENTS

| | | | |
|---|---|---|---|
| 2005162 | 9/1970 | Fed. Rep. of Germany | 564/44 |

OTHER PUBLICATIONS

Chem. Abst., 66, 65,149(n) (1967)–Moreno et al.

*Primary Examiner*—Douglas W. Robinson

*Attorney, Agent, or Firm*—Sprung, Felfe, Horn, Lynch & Kramer

[57] ABSTRACT

N-Cycloalkyl-N'-substituted-N'-acyl-ureas of the formula $$R^1\text{—NH—CO—}\underset{\displaystyle R^2}{\underset{|}{N}}\text{—CO—}R^3$$

in which $R^1$ is cycloalkyl, $R^2$ is cycloalkyl or optionally substituted phenyl, and $R^3$ is cycloalkyl or substituted phenyl, which are active against plant bacteria.

11 Claims, No Drawings

COMBATING BACTERIA WITH N-CYCLOALKYL-N'-SUBSTITUTED-N'-ACYL-UREAS

The invention relates to certain new substituted ureas, to a process for their preparation and to their use as plant bactericides.

It is known that certain copper compounds, for example copper oxychloride, have fungicidal and bactericidal properties. However, their action is not always satisfactory, especially in the case of low concentrations of active compound and when small amounts are applied.

The present invention now provides, as new compounds, the substituted ureas of the general formula $$R^1-NH-CO-\underset{\displaystyle R^2}{\underset{|}{N}}-CO-R^3 \qquad (I)$$

in which $R^1$ represents cycloalkyl, $R^2$ represents cycloalkyl or optionally substituted phenyl and $R^3$ represents cycloalkyl or substituted phenyl.

The compounds of the formula (I) are distinguished by a high activity against bacteria which are harmful to plants and are thus of interest as plant protection agents.

Surprisingly, the substituted ureas according to the invention exhibit a considerably more powerful bactericidal action than compounds of the same type of action which are known from the state of the art, for example copper oxychloride.

Preferred compounds of the formula (I) are those in which $R^1$ represents cyclohexyl, $R^2$ represents cyclohexyl or 2,6-dialkyl-phenyl with 1 to 4 carbon atoms per alkyl radical and $R^3$ represents cyclohexyl or represents phenyl carrying one or more substituents selected from $C_1$–$C_4$-alkyl, $C_1$–$C_4$-alkoxy, halogen, $C_1$–$C_2$-halogenoalkyl and nitro.

The invention also provides a process for the preparation of a substituted urea of the formula (I) in which a carbodiimide of the general formula $$R^1-N=C=N-R^2 \qquad (II),$$

in which $R^1$ and $R^2$ have the meanings indicated above, is reacted with a carboxylic acid of the general formula $$R^3-CO-OH \qquad (III),$$

in which $R^3$ has the meaning indicated above, if appropriate in the presence of a tertiary amine and if appropriate using a diluent.

If, for example, a dicyclohexyl-carbodiimide and 4-methoxy-benzoic acid are used as starting substances, the reaction of these compounds can be outlined by the following equation:

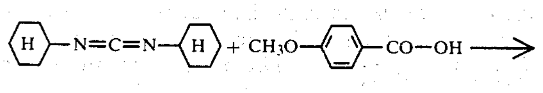

-continued

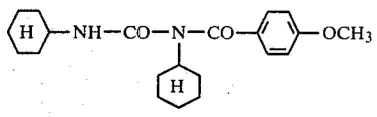

Formula (II) provides a definition of the carbodiimides to be used as starting substances. Preferably, in this formula, $R^1$ and $R^2$ represent those radicals which have been mentioned as preferred in the definition of the radicals $R^1$ and $R^2$ in formula (I).

Examples of the compounds (II) which may be mentioned are: dicyclohexyl-carbodiimide, N-(2,6-dimethyl-phenyl)-, N-(2,6-diethyl-phenyl)-, N-(2-methyl-6-ethyl-phenyl)-, N-(2,6-di-n-propyl-phenyl)-, N-(2,6-di-iso-propyl-phenyl)-, N-(2,6-di-n-butyl-phenyl)- and N-(2,6-di-iso-butyl-phenyl)-N'-cyclohexyl-carbodiimide.

The carbodiimides of the formula (II) are known compounds (see Methodicum Chimicum, Volume 6 (1974), pages 783–794, Georg-Thieme-Verlag Stuttgart and Academic Press New York, San Francisco, London). Their preparation from ureas or thioureas by splitting off water or hydrogen sulphide is also known. Toluenesulphonic acid chloride can be used as the condensing agent and hydrogen sulphide can be split off with lead carbonate. The carbodiimides can furthermore be obtained by reaction of cyclohexyl isocyanate with amines or anilines, water being split off.

Formula (III) provides a definition of the carboxylic acids also to be used as starting substances. Preferably, in this formula, $R^3$ has the meaning indicated as preferred in the definition of the radical $R^3$ in formula (I).

Examples of the carboxylic acids of the formula (III) which may be mentioned are: cyclohexanecarboxylic acid and 4-methyl-, 3-methyl-, 2-methyl-, 4-iso-propyl-, 4-tert.-butyl-, 4-methoxy-, 3-methoxy-, 2-chloro-, 3-chloro-, 4-chloro-, 2,4-dichloro-, 2,5-dichloro-, 3,4-dichloro-, 2,6-dichloro, 2-bromo-, 3-bromo-, 4-bromo-, 3-fluoro-, 4-fluoro-, 2-chloro-5-bromo-, 3-trifluoromethyl-, 2-nitro-, 3-nitro-, 4-nitro-, 5-chloro-2-nitro-, 4-chloro-3-nitro-, 2-methyl-3-nitro-, 3-methyl-2-nitro-, 3-methyl-4-nitro-, 4-methyl-3-nitro- and 5-methyl-2-nitrobenzoic acid.

The carboxylic acids of the formula (III) are generally known compounds customary in the laboratory.

The process for the preparation of the substitued ureas of the formula (I) is preferably carried out using a suitable solvent or diluent. Possible solvents and diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; nitriles, such as acetonitrile and propionitrile; and alcohols, such as methanol, ethanol and n- and isopropanol.

Examples of tertiary amines which can be employed as catalysts in the process according to the invention are trimethylamine, triethylamine, ethyl-di-isopropylamine, ethyl-di-cyclohexylamine, N,N-dimethylaniline, N,N-dimethyl-benzylamine and diaza-bicyclononane.

The reaction temperature can be varied within a substantial range. In general, the reaction is carried out at temperatures from 0° to 150° C., preferably at 20° to 100° C.

The process according to the invention is in general carried out under normal pressure.

The starting substances are usually employed in equimolar amounts for carrying out the process according to the invention. An excess of one or the other of the reactants brings no significant advantages. The reaction is in general carried out in a suitable diluent in the presence of a tertiary amine, and the reaction mixture is stirred at the required temperature for several hours. After distilling off the solvent in vacuo, the products are in general obtained in crystalline form. The melting point is used for characterization of the products, which are usually purified by recrystallization.

The active compounds according to the invention exhibit a powerful microbicidal action and can be employed in practice for combating undesired micro-organisms. The active compounds are suitable for use as plant protection agents and can be employed as bactericides.

Bactericidal agents are employed in plant protection for combating Pseudomonadaceae, Rhizobiaceae, Enterobacteriaceae, Corynebacteriaceae and Streptomycetaceae.

Thus, the active compounds according to the invention exhibit an action against *Xanthomonas oryzae* in rice. In addition to an action after application to the leaves, the present compounds also have a significant systemic action, which can be detected after application to irrigation water or to the soil.

The good toleration, by plants, of the active compounds, at the concentrations required for combating plant diseases, permits treatment of above-ground parts of plants, of vegetative propagation stock and seeds, of the soil and of irrigation water.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of in general 0.001 to 50 g, preferably 0.01 to 10 g, are generally employed per kilogram of seed.

For the treatment of soil, active compound concentrations of in general 0.00001 to 0.1% by weight, preferably 0.0001 to 0.02%, are employed at the place of action.

The present invention also provides bactericidal compositions containing as active ingredient a compound of the present invention in admixture with a solid or liquefied gaseous diluent or carrier or in admixture with a liquid diluent or carrier containing a surface-active agent.

The present invention also provides a method of combating bacteria (especially phytopathogenic bacteria) which comprises applying to the bacteria, or to a habitat thereof, a compound of the present invention alone or in the form of a composition containing as active ingredient a compound of the present invention in admixture with a diluent or carrier.

The present invention further provides crops protected from damage by bacteria by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples

EXAMPLE 1

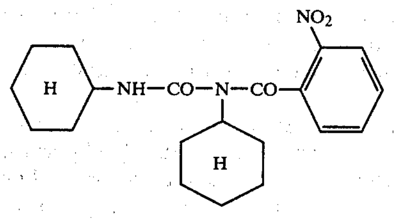

(1)

A solution of 25 g (0.15 mol) of 2-nitro-benzoic acid in 75 ml of methanol was added dropwise to a boiling solution of 31 g (0.15 mol) of dicyclohexyl-carbodiimide and 8 ml of triethylamine in 300 ml of methanol. The reaction mixture was heated under reflux for 2 hours and stirred at room temperature overnight. After distilling off the solvent in vacuo, the residue was recrystallized from isopropanol. 25 g (45% of theory) of N-(2-nitrobenzoyl)-N,N'-dicyclohexyl-urea of melting point 134° C. were obtained.

The following compounds of the formula (Ia) could be prepared analogously:

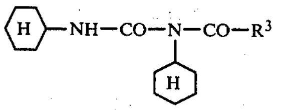

(Ia)

| Compound No. | $R^3$ | Melting point (°C.) | Yield (% of theory) |
|---|---|---|---|
| 2 | 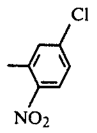 | 166 | 33 |
| 3 | 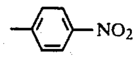 | 204 | 86 |
| 4 | 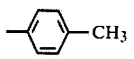 | 133 | 41 |
| 5 | 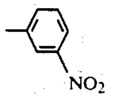 | 175 | 56 |

-continued

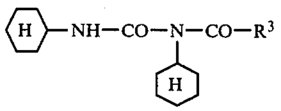

(Ia)

| Compound No. | $R^3$ | Melting point (°C.) | Yield (% of theory) |
|---|---|---|---|
| 6 | 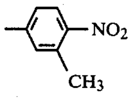 | 190 | 55 |
| 7 | 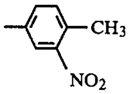 | 175 | 52 |
| 8 | 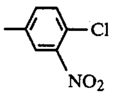 | 180 | 47 |
| 9 | 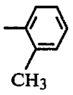 | 143 | 70 |
| 10 | 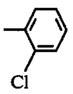 | 167 | 63 |
| 11 | 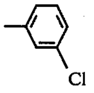 | 175 | 50 |
| 12 | 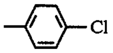 | 175 | 55 |
| 13 | 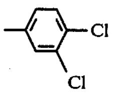 | 189 | 68 |
| 14 | 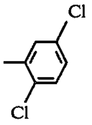 | 177 | 43 |
| 15 | 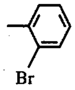 | 154 | 38 |
| 16 | 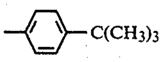 | 162 | 42 |
| 17 | 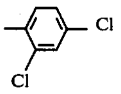 | 154 | 59 |
| 18 | 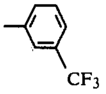 | 165 | 40 |
| 19 | 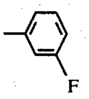 | 165 | 58 |
| 20 | 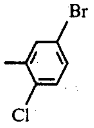 | 177 | 47 |

-continued

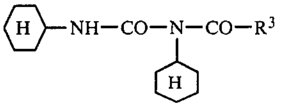

(Ia)

| Compound No. | $R^3$ | Melting point (°C.) | Yield (% of theory) |
|---|---|---|---|
| 21 | 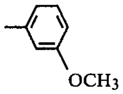 | 145 | 43 |
| 22 | 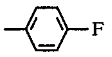 | 178 | 48 |
| 23 | 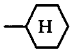 | 148 | 62 |
| 24 | 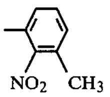 | 158-62 | 65 |
| 25 | 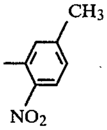 | 176-80 | 53 |
| 26 | 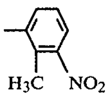 | 176-81 | 57 |

EXAMPLE 2

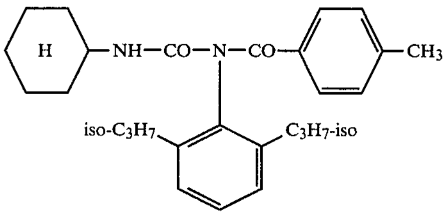

(27)

The compound was obtained analogously to Example 1, in a yield of 17% of theory. The melting point was 238° C.

The bactericidal activity of the compounds of this invention is illustrated by the following examples; the compounds according to the present invention are each identified by the number (given in brackets) from the examples hereinabove:

EXAMPLE 3

*Xanthomonas oryzae* test/bacteriosis/rice

To produce a suitable preparation of active compound, 1 part by weight of active compound was mixed with 25 parts by weight of a solvent (acetone) and 0.75 part by weight of a dispersing agent (alkylaryl polyglycol ether), and the concentrate was diluted with water to the desired concentration.

Rice plants of the variety Kinmaze which were four weeks old were sprayed with the spray liquid until dripping wet and allowed to dry and the plants were inoculated with *Xanthomonas oryzae* by dipping needles into an aqueous suspension of the bacteria and pricking the leaves.

After incubation at 100% relative atmospheric humidity for 48 hours, the plants remained in a greenhouse at 24° to 26° C. and 70 to 80% relative atmospheric humidity for 10 days until they were examined. The degree of infection was expressed in percent of the infection of the untreated control plants: 0% denoted no infection and 100% corresponded to the infection of the control plants.

In this test, for example, the following compounds showed a superior action compared with the prior art: compounds (6) and (7).

EXAMPLE 4

*Xanthomonas oryzae* test/bacteriosis/rice/systemic

To produce a suitable preparation of active compound, 1 part by weight of active compound was mixed with 125 parts by weight of a solvent (acetone) and 3.75 parts by weight of a dispersing agent (alkylaryl polyglycol ether), and the concentrate was diluted with water to the desired concentration.

Pots 10×10 cm in size which contained rice plants of the variety Kinmaze which were about 5 weeks old were watered with a definite amount of this preparation of active compound, the amount of active compound to be applied being calculated from the surface area of the soil.

3 days after treatment of the soil, the plants were inoculated with *Xanthomonas oryzae* by dipping needles into an aqueous suspension of the bacteria and pricking the leaves. The plants remained in a greenhouse at 24° to 26° C. and 70 to 80% relative atmospheric humidity until they were examined.

The degree of infection was expressed in percent of the infection of the untreated control plants: 0% denoted no infection and 100% corresponded to the infection of the control plants.

In this test, the following compounds showed a superior action compared with the prior art: compounds (1), (4), (7), (8) and (9).

It will be appreciated that the instant specification and examples are set forth by way of illustration and not limitation, and that various modifications and changes may be made without departing from the spirit and scope of the present invention.

We claim:

1. An N-cycloalkyl-N'-substituted-N'-acyl-urea of the formula $$R^1—NH—CO—\underset{R^2}{\underset{|}{N}}—CO—R^3$$

in which $R^1$ is cyclohexyl, $R^2$ is cyclohexyl, phenyl or di-$C_{1-4}$-alkyl substituted phenyl, and $R^3$ is cyclohexyl, phenyl substituted by $C_{1-4}$-alkyl, $C_{1-4}$-alkoxy, halogen or $C_{1-2}$-haloalkyl, or phenyl substituted by nitro plus at least one member selected from the group consisting of $C_{1-4}$-alkyl, $C_{1-4}$-alkoxy, halogen or $C_{1-2}$-haloalkyl.

2. A compound according to claim 1, in which $R^2$ is cyclohexyl or 2,6-dialkyl-phenyl.

3. A compound according to claim 1, in which said compound is N-(4-methylbenzoyl)-N,N'-dicyclohexylurea of the formula

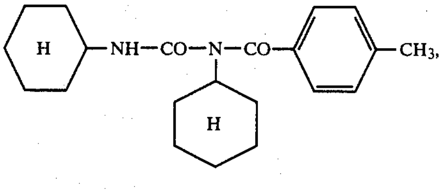

4. A compound according to claim 1, in which said compound is N-(3-nitrobenzoyl)-N,N'-dicyclohexyl-urea of the formula

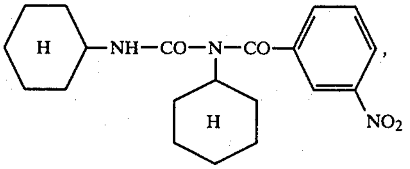

5. A compound according to claim 1, in which said compound is N-(4-methyl-3-nitrobenzoyl)-N,N'-dicyclohexyl-urea of the formula

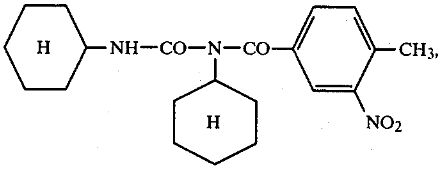

6. A compound according to claim 1, in which said compound is N-(4-chloro-3-nitrobenzoyl)-N,N'-dicyclohexyl-urea of the formula

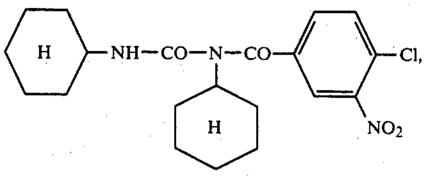

7. A compound according to claim 1, in which said compound is N-(4-fluorobenzoyl)-N,N'-dicyclohexyl-urea of the formula

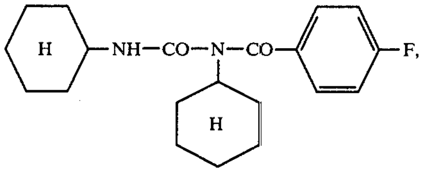

8. A compound according to claim 1, in which said compound is N-cyclohexylcarbonyl-N,N'-dicyclohexyl-urea of the formula

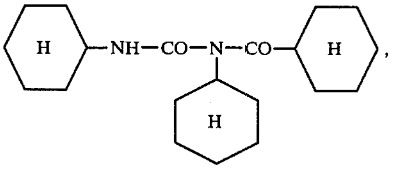

9. A bactericidal composition containing an active ingredient a bactericidally effective amount of a compound of the formula

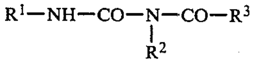

in which $R^1$ is cyclohexyl, $R^2$ is cyclohexyl, phenyl or di-$C_{1-4}$-alkyl substituted phenyl, and $R^3$ is cyclohexyl or phenyl substituted by $C_{1-4}$-alkyl, $C_{1-4}$-alkoxy, halogen or $C_{1-2}$-haloalkyl or phenyl substituted by nitro plus at least one member selected from the group consisting of $C_{1-4}$-alkyl, $C_{1-4}$-alkoxy, halogen or $C_{1-2}$-haloalkyl, in admixture with a diluent.

10. A method of combating bacteria which comprises applying to the bacteria, or to a habitat thereof, a bactericidally effective amount of a compound of the formula

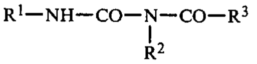

in which $R^1$ is cyclohexyl, $R^2$ is cyclohexyl, phenyl or di-$C_{1-4}$-alkyl substituted phenyl, and $R^3$ is cyclohexyl or phenyl substituted by $C_{1-4}$-alkyl, $C_{1-4}$-alkoxy, halogen or $C_{1-2}$-haloalkyl or phenyl substituted by nitro plus at least one member selected from the group consisting of $C_{1-4}$-alkyl, $C_{1-4}$-alkoxy, halogen or $C_{1-2}$-haloalkyl.

11. The method according to claim 10, in which said compound is

N-(4-methylbenzoyl)-N,N'-dicyclohexyl-urea,

N-(4-methyl-3-nitrobenzoyl)-N,N'-dicyclohexyl-urea,

N-(4-chloro-3-nitrobenzoyl)-N,N'-dicyclohexyl-urea,

N-(4-fluorobenzoyl)-N,N'-dicyclohexyl-urea, or

N-cyclohexylcarbonyl-N,N'-dicyclohexyl-urea.

* * * * *